United States Patent
Helal

(10) Patent No.: US 7,155,202 B2
(45) Date of Patent: Dec. 26, 2006

(54) PORTABLE DEVICE MEDICAL ASSISTANT

(75) Inventor: Abdelsalam A. Helal, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 135 days.

(21) Appl. No.: 10/889,161

(22) Filed: Jul. 12, 2004

(65) Prior Publication Data

US 2005/0038860 A1   Feb. 17, 2005

Related U.S. Application Data

(60) Provisional application No. 60/486,018, filed on Jul. 10, 2003, provisional application No. 60/490,717, filed on Jul. 29, 2003.

(51) Int. Cl.
- H04M 11/04 (2006.01)
- G08B 1/08 (2006.01)
- G08B 5/22 (2006.01)
- H04L 7/00 (2006.01)
- G09B 21/00 (2006.01)

(52) U.S. Cl. .............. 455/404.1; 340/573.1; 340/539.25; 340/825.19; 340/825.36; 340/825.49

(58) Field of Classification Search .......... 455/404.1, 455/41.2, 404.2, 550.1; 340/573.1, 539.12, 340/539.16, 539.13, 41.2, 539.25, 565, 573.4, 340/825.19, 825.49, 825.36; 607/300, 506, 607/360, 508, 517, 32, 500; 379/40; 348/14.16, 348/14.01

See application file for complete search history.

(56) References Cited

U.S. PATENT DOCUMENTS

| | | |
|---|---|---|
| 5,833,603 A | 11/1998 | Kovacs et al. |
| 5,872,834 A | 2/1999 | Teitelbaum |
| 6,204,763 B1 | 3/2001 | Sone |
| 6,305,377 B1 | 10/2001 | Portwood et al. |
| 6,362,778 B1 | 3/2002 | Neher |
| 6,380,858 B1 | 4/2002 | Yarin et al. |
| 6,404,880 B1 | 6/2002 | Stevens |
| 6,428,475 B1 | 8/2002 | Shen |
| 6,453,027 B1 | 9/2002 | Kang et al. |
| 6,496,111 B1 | 12/2002 | Hosack |
| 6,553,262 B1 | 4/2003 | Lang et al. |
| 6,567,672 B1 | 5/2003 | Park et al. |
| 6,604,650 B1 | 8/2003 | Sagar |
| 6,678,516 B1 | 1/2004 | Nordman et al. |
| 6,774,784 B1 * | 8/2004 | Satoh .................. 340/506 |
| 6,774,795 B1 | 8/2004 | Eshelman et al. |
| 6,980,112 B1 * | 12/2005 | Nee ..................... 340/573.1 |

(Continued)

OTHER PUBLICATIONS

Mann, W., et al., "Smart Phones for the Elders: Boosting the Intelligence of Smart Homes", Am. Assoc. for Artificial Intell. (AAAI), (Jul. 2002).

(Continued)

Primary Examiner—Melody Mehrpour
(74) Attorney, Agent, or Firm—Akerman Senterfitt

(57) ABSTRACT

The present invention provides a device, a method, and a machine readable storage for managing a material substance program. The device can include a portable computing device having mobile telephony capabilities and a portable computing device having mobile telephony capabilities; and a wireless identification device communicably coupled to the portable computing device for identifying materials. The method for managing a material substance program can include scanning a material source to identify a material identifier, sending the material identifier to a proxy server, receiving material information from the proxy server, and displaying material information on a portable computing device having mobile telephony capabilities.

14 Claims, 3 Drawing Sheets

U.S. PATENT DOCUMENTS

| | | |
|---|---|---|
| 2001/0046862 A1 | 11/2001 | Coppinger et al. |
| 2002/0060243 A1 | 5/2002 | Janiak et al. |
| 2002/0127145 A1 | 9/2002 | Der Ghazarian et al. |
| 2002/0128864 A1 | 9/2002 | Maus et al. |
| 2003/0009088 A1 | 1/2003 | Korth et al. |
| 2003/0013507 A1 | 1/2003 | Sato |
| 2003/0064732 A1 | 4/2003 | McDowell et al. |
| 2003/0064749 A1 | 4/2003 | Soini et al. |
| 2003/0083020 A1 | 5/2003 | Langford |
| 2003/0087628 A1 | 5/2003 | Michibata |
| 2005/0038673 A1* | 2/2005 | Stookey et al. ............ 705/2 |
| 2005/0101250 A1* | 5/2005 | Helal et al. ............ 455/41.2 |

OTHER PUBLICATIONS

Haigh, K., et al., "The Role of Intelligent Technology in Elder Care", AAAI-02 WS on Automation as Caregiver, (Jul. 2002).

Giraldo, C., "mPCA-A Mobile Patient Care-Giving Assistant for Alzheimer Patients", UbiCog '02, (Sep. 29, 2002).

Helal, S., et al., "Smart Phone Based Cognitive Assistant", UbiHealth, (Oct. 12-15, 2003).

Helal, S., et al., "Assistive Environments for Successful Aging". UbiComp 2003, no month listed.

Helal, S., et al., "Enabling Location-Aware Pervasive COmputing Applications for the Elderly", IEEE Conf. on Pervasive Computing & Comm. PerCom '03, no month listed.

Helal, S., et al., "Assistive Environments for Elder Care—Integrating Smart Phones with Smart Homes", ICADI Conf. on Aging, (2003), no month listed.

Long, M., "A New Reference Design for Jumpstarting Smartphone Development", E-inSITE, (Feb. 13, 2003).

"Home Automation Systems", National Security, Inc., Internet, viewed (Jun. 3, 2003).

"SmartPhones", Motorola, Internet, (viewed Jun. 3, 2003).

"An Executive White Paper—Secure Mobile Banking Architecture", Consumer Direct Link, Inc., (Sep. 2001).

Paron MPC, Consumer Direct Link, Inc., (2000-2001), no month listed.

* cited by examiner

PORTABLE DEVICE MEDICAL ASSISTANT

CROSS-REFERENCE TO RELATED APPLICATIONS

This application claims the benefit of both U.S. Provisional Application Ser. No. 60/486,018, filed in the United States Patent and Trademark Office on Jul. 10, 2003, and 60/490,717 filed in the United States Patent and Trademark Office on Jul. 29, 2003, the entirety of both applications is incorporated herein by reference.

BACKGROUND

1. Field of the Invention

The present invention relates to the field of portable computing devices and, more particularly, to a portable communication device and method for providing medical assistance.

2. Description of the Related Art

With the ever rising costs of medical care, there is a need for providing detailed medical assistance that is cost effective, yet still comprehensive. For years, many medical providers and seekers have turned to "live-in" nurses or nurses that make home visits on a daily basis to provide routine medical care and monitoring. Although such methods have enjoyed some success, the overall costs, and even effectiveness, of such models has left a void.

As communications systems have advanced, the void has been filled by some devices. For instance, devices have been manufactured that can initiate an emergency signal to emergency services when activated by the user. A user may initiate such a signal when the user has been injured in a fall and cannot resume normal movement.

Although helpful, such a device has severe limitations. One limitation is that the device is not an "aware" or "smart" device in that the device must rely on user input. The device only signals the emergency service when the user activates the device for that purpose. Further, the device merely acts as conduit for communication between the user and the emergency services. Such a device cannot provide the user with any helpful information, and more importantly, the device cannot provide the emergency service with any vital information that could possibly be used to save the user's life.

Although hospitals have provided systems to monitor a patient's biometric statistics, the monitoring typically requires a patient to be bedridden for effective monitoring. Additionally, the monitoring of the different substances and materials prescribed to a patient is typically monitored by a nurse and/or doctor. Nevertheless, the misallocation and the improper prescription of materials to patients results in multiple accidents on a yearly basis. These accidents can be life threatening or worse and can expose insurance companies to great liability.

Therefore, there exists a need for a material management program that can prevent the misallocation and/or improper prescription of materials. Further, this need not only exists in the hospital, but also exists outside of the hospital environment.

SUMMARY OF THE INVENTION

The present invention provides a device and method for managing a material substance program. The device and method can provide the user and/or caretaker with multiple reminders for consuming materials at appropriate times. Further, the device and method can also provide material information, such as specialized instructions, side affects, and the like. Although such a material substance program may commonly be limited to the use and monitoring of prescription drugs, the invention is not limited in this regard as "materials" can include any consumable substance such as herbs, vitamins, foods, transdermal drugs, intravenous drugs, and oral drugs.

In one embodiment, a device for managing a material substance program can include a portable computing device having mobile telephony capabilities and a wireless identification device communicably coupled to the portable computing device for identifying materials. The wireless identification device can be one or more of a bar code reader, a radio frequency identification mechanism, and a combination thereof. The portable computing device can also include one or more of a display screen, an audible transducer, a vibration mechanism, and a combination thereof. Additionally, the portable computing device can include memory for storing material information.

In one embodiment, a method for managing a material substance program can include the steps of scanning a material source to identify a material identifier, sending the material identifier to a proxy server, and receiving material information from the proxy server. Also, the method can include the step of displaying material information on a portable computing device having mobile telephony capabilities.

In another arrangement, the method can include the step of programming a material notification in accordance with the material information. Also, the material notifications can be provided with a portable computing device having mobile telephony capabilities. Further, providing material notifications can include one or more of displaying material information, audibly conveying the material information, initiating vibration of the portable computing device, and a combination thereof.

Still further, the method can include the step receiving user confirmation that a material was consumed. Additionally, the material quantity can be tracked in accordance with consumption and material can be ordered in accordance with the material quantity.

In one embodiment, a machine-readable storage can be provided. The machine readable code can have stored thereon, a computer program having a plurality of code sections, where the code sections are executable by a machine for causing the machine to perform the steps of the method.

BRIEF DESCRIPTION OF THE DRAWINGS

There are shown in the drawings, embodiments that are presently preferred; it being understood, however, that the invention is not limited to the precise arrangements and instrumentalities shown.

DETAILED DESCRIPTION OF THE INVENTION

Figure 1:
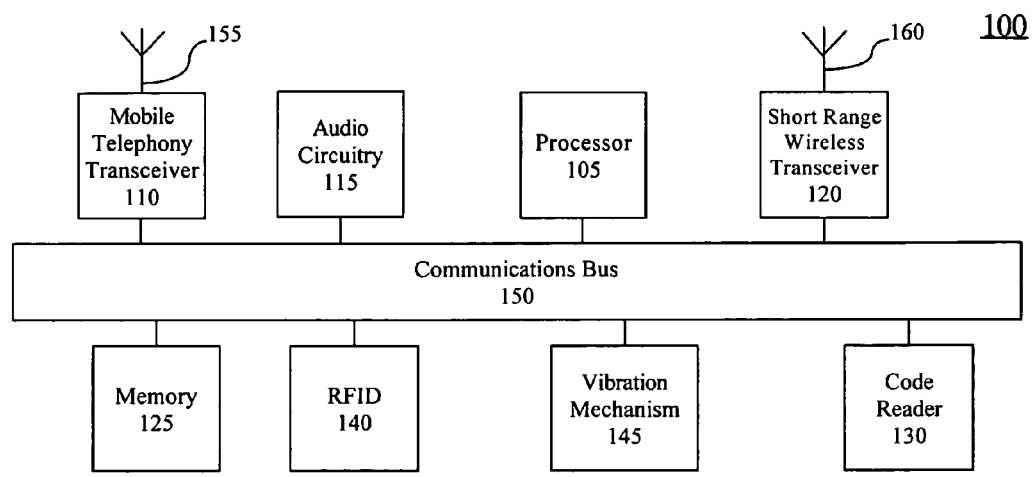
FIG. 1 is a schematic diagram illustrating an exemplary portable communications device (PCD) configured in accordance with the inventive arrangements disclosed herein.

FIG. 1 is a schematic diagram illustrating an exemplary portable computing device (PCD) 100 for managing a material substance program. Although such a material substance program may be commonly limited to the use and monitoring of prescription drugs, the invention is not limited in this regard as "materials" can include any consumable substance such as herbs, vitamins, foods, transdermal drugs, intravenous drugs, and oral drugs. The PCD 100 can be used by a patient or health care provider to manage, control, and monitor the timeliness of the patient's consumption of materials and can manage the inventory of those materials. The PCD 100 can be any suitably configured portable computing device, such as a mobile phone, a personal digital assistant, and a tablet personal computer. The PCD 100 can be configured in accordance with the inventive arrangements disclosed herein.

As shown, the PCD 100 can include a processor 105, a mobile telephony transceiver 110, audio circuitry 115, a short range wireless transceiver 120, memory 125, and a wireless identification device, such as a code reader 130 and/or a radio frequency identification (RFID) mechanism 140. Each of the aforementioned components can be communicatively linked via a suitable communications bus 150. Further, it should be noted that PCD 100 can include all of the components listed above, or various combinations thereof, and that other hardware or software components can be incorporated to extend or enhance the functionality of the PCD 100.

A suitable operating system can be provided that controls the allocation and usage of the component resources, such as memory 125, processor 105, and the other components of the PCD 100. Further, one or more applications compatible with the operating system can also be provided for controlling the various functions of the PCD 100. Thus, the processor 105 can include an operating system which can support the execution of one or more applications intended to run on that platform and which support operation of the various functions and features disclosed herein.

For instance, the PCD 100 can include the Java 2 Platform, Micro Edition (J2ME®) that has programming specifications and a virtual machine, such as the K Virtual Machine, which allows a J2ME-encoded programs to run on the PCD 100. Depending upon the functionality required by the software and the hardware configuration of the PCD 100, the PCD 100 can include the Connected Limited Device Configuration (CLDC) or and the Connected Device Configuration (CDC). The CLDC lays out the application program interface (API) and virtual machine features needed to support the PCD 100. The CDC extends the functionality of the CLDC by including the Mobile Information Device Profile (MIDP), which adds midlets, a user interface, networking, and messaging details for interfacing with the PCD 100.

The memory 125 can be a data storage structure that accepts information for storage in electrical, mechanical, or magnetic form. Examples of memory 125 can include random access memory (RAM), read-only memory (ROM), programmable ROM (PROM), erasable programmable ROM (EPROM), or any other type of memory suitable for use within a portable computing device such as the PCD 100 or a device having mobile telephony capabilities, such as a cellular telephone. It should be appreciated that the memory 125, although illustrated as a separate component, can be incorporated into the processor 105 or another component.

In any arrangement, the memory 125 can include programmatic instructions to be executed by the processor 105 as well as any operational data necessary for operation of the PCD 100. For instance, the memory 125 can store operational information, such as when a user consumes, or fails to consume, a material. The memory can also store material information, such as general information, usage directions, warnings for material interactions, and the like. As will be discussed in detail below, the memory 125 can be updated over time. Still further, it should be noted that in some arrangements, the memory 125 can be removed and/or supplemental memory 125 can be added. The supplemental memory 125 can simply provide a greater storage capacity and/or can provide particular data or programmatic functions stored on the supplemental memory 125 to extend the functionality of the PCD 100.

Wireless signals can be received and sent via the antenna 155 which can be configured for longer-range communications, such as mobile telephony communications. For instance, the PCD 100 can be configured to wirelessly communicate over CDMA (code-division multiple access), TDMA (time division multiple access), GSM (Global System for Mobile Communication) networks, or the like. Accordingly, the antenna 155 can be operatively connected to the mobile telephony transceiver 110 and signals detected by antenna 155 can be provided to the mobile telephony transceiver 110 for processing and decoding. For example, the mobile telephony transceiver 110 can include a codec for coding and decoding information received or to be sent via wireless transmission. The mobile telephony transceiver 110 can make the decoded signals and/or information available to other components of the PCD 110 for processing. Outbound information received by the mobile telephony transceiver 110 can be coded and/or formatted for wireless transmission by the codec and then provided to the antenna 155 for transmission.

It should be appreciated that the PCD 100 can communicate via conventional mobile telephony calls and access wireless networks, for example using Wireless Access Protocol (WAP) or another suitable wireless communications protocol. Accordingly, the PCD 100 can access the Internet, the Web, a Local Area Network (LAN), and/or a wide area network (WAN) to transmit and receive information regarding the user, general information regarding the material management, and/or information regarding particular materials. Thus, it should be noted that voice over internet protocol (VoIP) services can be accessed over such wireless networks. Still further, access via a wireless communications link to any of the above mentioned networks, or servers within those networks, can provide access to any applications and/or services disposed on such networks.

The audio circuitry 115 can be communicably coupled to an audible transducer (see 225 in FIG. 2), such as a microphone, speaker, or other transducive element for receiving and/or generating sound, and one or more analog-to-digital converters for digitizing the received sound. The audio circuitry 115 further can include one or more digital-to-analog converters for converting digital information into sound. The audio circuitry 115 can further include one or more amplifiers. Notably, although not shown, the PCD 100 can include one or more audio output jacks and/or or other digital data interface ports.

It should be appreciated that the audio circuitry 115 can include additional processors, such as digital signal processors (DSP) as may be required for processing audio and performing functions such as audio encoding, audio decoding, noise reduction, and the like. For example, according to one embodiment of the present invention, the audio circuitry 115 can be implemented using one or more discrete components. In another arrangement, the audio circuitry 115 can be implemented using one or more larger integrated circuits configured to perform the various functions disclosed herein. Thus, the PCD 100 can be configured to play various audio formats from streaming formats to MP3's, or other audio file formats such as .WAV or .AIFF files.

The PCD 100 also can include a short range wireless transceiver 120 as well as an antenna 160 operatively connected thereto. The short range wireless transceiver 120 can both send and receive data. For example, according to one embodiment of the present invention, the short range wireless transceiver 120 can be implemented as a Blue-Tooth-enabled wireless transceiver, or as a transceiver configured to communicate with one of the 802.11 family of short range wireless communications specifications. The short range wireless transceiver 120 and accompanying antenna 160 can be configured to communicate using any of a variety of short range, wireless communications protocols and/or systems. Accordingly, the various examples disclosed herein have been provided for illustration only and should not be construed as a limitation of the present invention.

The PCD 100 can include a plurality of scanning devices such as a code reader 130 and a RFID mechanism 140. The code reader 130 can be an optical device capable of reading various coding schemes such as bar codes, or other visual patterns, including, but not limited to, single and/or multi-dimensional bar codes. The code reader 130 can include a scanning device capable of directing a beam of light across the visual code and measuring the amount of light that is reflected back, as dark areas reflect less light than white or lighter areas. The scanning device converts the light energy into electrical energy, which is then converted to data by a codec. As an example, the code reader 130 can be configured to read a bar code present on material packaging, such as a universal product code (UPC) commonly printed on over the counter drug packaging. Accordingly, by using the PCD 100, the caretaker or the patient can confidently identify a particular material and prevent the misidentification of that material.

Another suitable scanning device is an RFID mechanism 140. The RFID mechanism 140 incorporates the use of electromagnetic or electrostatic coupling in the radio frequency (RF) portion of the electromagnetic spectrum to uniquely identify an object, animal, or person. The RFID mechanism 140 does not require direct contact or line-of-sight scanning. An RFID mechanism 140 can include an antenna and transceiver (often combined into one reader) for use with a transponder (the tag) that can be incorporated with material packaging and/or a material container. The antenna uses radio frequency waves to transmit a signal that activates the transponder. When activated, the tag transmits data, which can include various identification and/or other information, back to the antenna Among other things, the data is used to notify a programmable logic controller, such as the processor 105, that an action should occur. For example, the action can include any programmatic response such initiating communications to interface and exchange data with another computing system, or simply providing the user with information regarding a particular material. The PCD 100 can include a low-frequency RFID mechanism 140 of approximately 30 KHz to 500 KHz having a short transmission range of approximately six feet, or a high-frequency RFID mechanism 140 of approximately 850 MHz to 950 MHz and 2.4 GHz to 2.5 GHz and having a longer transmission range of approximately 90 feet or more.

Any of a variety of RFID mechanisms can be used. As such, the present invention is not limited by the various examples disclosed herein.

A variety of other components and sensors (not shown), such as biometric sensors and a global positioning system module that can be used to determine the location of a user in an emergency event, can be included with PCD 100. Also, an infrared transceiver can be incorporated into the device for communication with other devices so configured. According to one embodiment of the present invention, a conventional telephone jack or port can be included in the PCD 100 such that a user need only plug the PCD 100 into a standard wall jack to initiate telephone calls over the Public Switched Telephone Network (PSTN). Similarly, a port can be provided so that the user can plug the PCD 100 into a device, such as a computer or server, providing wired VoIP services. Such arrangements can be advantageous in situations where mobile telephony connectivity may not be available or is intermittent.

Each of the various components of the PCD 100 disclosed herein can be communicatively linked with one another using appropriate circuitry, whether through the memory 125, one or more additional memories (not shown), the processor 105, one or more additional interface processors or logic controllers (not shown), and/or the communications bus 150. For example, while most of the components described herein are depicted as being linked to the communications bus 150, it should be appreciated that each sensor can be configured to communicate with the processor 105 through a suitable interface.

Additionally, the various components disclosed herein can be embodied in other forms. The configuration disclosed and described with reference to FIG. 1 is provided for purposes of illustration only. For example, the various components can be implemented as one or more discrete components, as one or more processors, logic controllers, and/or DSP's, or any combination thereof.

Figure 2:
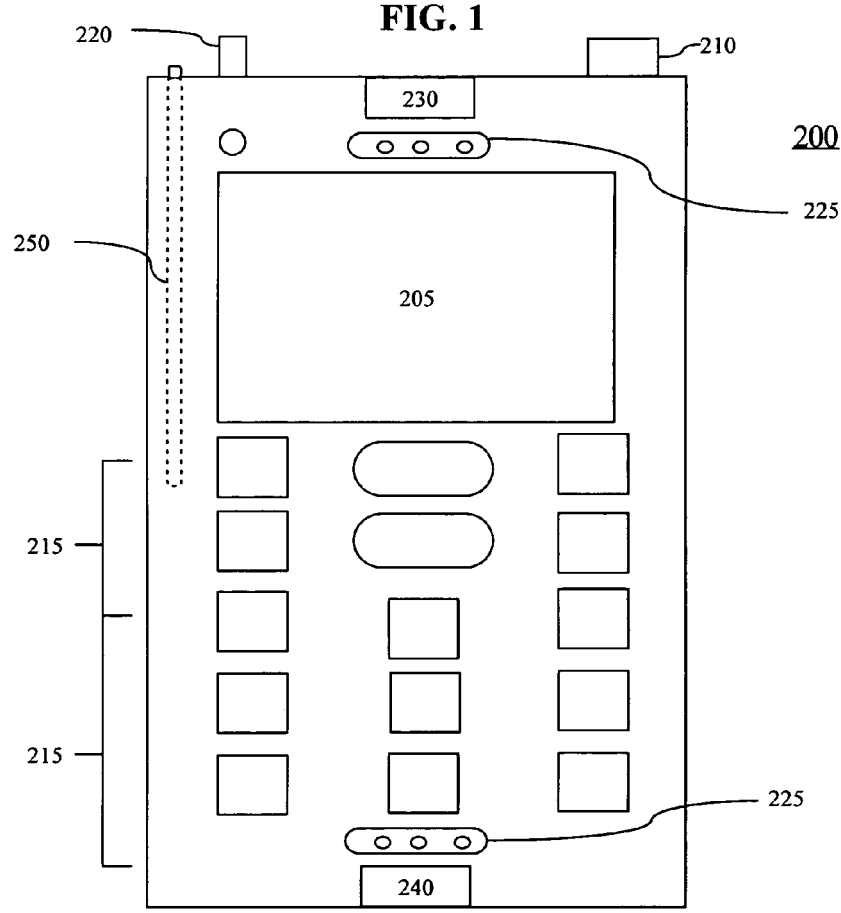
FIG. 2 is a schematic diagram illustrating a PCD in accordance with the inventive arrangements disclosed herein.

FIG. 2 is a schematic diagram illustrating an exemplary PCD 200 having mobile telephony capabilities. As shown, the PCD 200 can include a display screen 205, one or more control or operational keys 215, which can include special function command keys for operation of one or more of the functions disclosed herein, alphanumeric keys or buttons 215, and a short range antenna 220 and a mobile telephony antenna 210 (both of which may be configured to be fully located within the PCD 200). The PCD 200 can also include one or more transducers 225 for receiving sound and/or generating audible notifications and a vibration mechanism (not shown) for providing vibration notifications. The PCD 200 further can include a battery or other power source (not shown).

The physical arrangement of the PCD 200 has been provided for purposes of illustration only. As such, it should be appreciated that the various components can be located in any of a variety of different configurations. For example, the PCD 200 can include additional keys or controls disposed on the frontal portion or the sides of the unit. Further, the PCD 200 can also include detachable components, such as a stylus 250, for operating the PCD 200. Additionally, the PCD 200 can have a suitable power source such as a removable and rechargeable battery.

According to one embodiment of the present invention, the physical arrangement of the PCD 200 can be conducive for use by older persons or those that may have difficulty accessing and/or operating the various keys and/or controls of conventional mobile telephones, such as persons with physical disabilities or other infirmities. For instance, the control keys 215 and the alphanumeric keys 215 can be larger for ease of use. Similarly, the display screen 205, such as a liquid crystal display (LCD), can be larger than those found on conventional mobile telephony devices and have an increased contrast ratio. Also, a combination of the control keys 215 can be used to change the resolution of the screen to enable users with limited sight to clearly see information displayed on screen 205. It should be appreciated that any of a variety of different display screens, including touchscreens, can be used within the PCD 200.

As noted, the PCD 200 can include a variety of wireless identification devices, such as a bar code reader 230 and a RFID mechanism 240. Although the bar code reader 230 and the RFID mechanism 240 are shown as being integrated with the PCD 200, they can be located on detachable devices for remote use. As an example, such a device may be suitably configured with the Blue-Tooth protocol for wireless communication over the short range wireless transceiver 220 or be linked via a wired connection.

In addition to the components and hardware discussed above, the PCD 200 can be programmed with calendaring software that can, among other functions, program and provide material notifications in accordance with the material information. For instance, the calendaring software can provide notifications to the user to take a medicine at a particular time, on a daily basis. The notifications can be provided by displaying a message on the display 205 of the PCD 200, by generating an audible reminder, and/or by vibrating. Additionally, the calendaring software of the PCD 200 can not only provide notifications that a material should be consumed, but also record the consumption of the material. Still further, the PCD 200 can track the inventory of materials and order replacement inventory as necessary.

Figure 3:
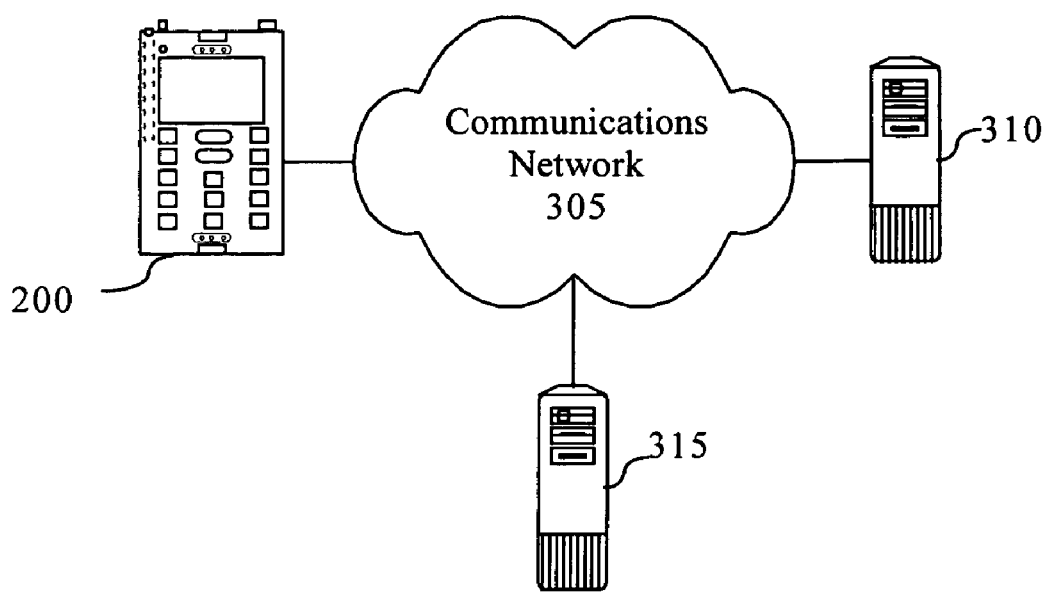
FIG. 3 is a schematic diagram illustrating an exemplary system for supporting a PCD in accordance with the inventive arrangements disclosed herein.

FIG. 3 is a schematic diagram illustrating an exemplary system 300 supporting a PCD 200 and its various uses and applications as disclosed herein. The PCD 200 can be designed for individuals and/or caretakers managing a health care program, such as the delivering and monitoring of daily medicinal and/or nutritional consumption. Notably, the PCD 200 can be communicatively linked to the communications network 305 via any suitable connection, whether wireless or wired. The system can also include a proxy server 315, such as a local computing device, and a material supply server 310, which may be affiliated with a material supply, such as a pharmacy. The PCD 200, the proxy server 315, and the material supply server 310 can be communicatively linked via a communications network 305. It should be noted that the proxy server 315 and the supply server 310 can include Java 2 Platform, Standard Edition (J2SE), or the Java 2 Platform, Enterprise Edition (J2EE), or any other suitable processing or communications platform. Suitable data base software can also be provided.

The PCD 200, or the client, can scan a material package and or container to identify the material and/or obtain other material information. For instance, a bar code reader can obtain a variety of information from a 3-D bar code, such as a material identifier, material manufacture date, expiration date, prescription number, and even pharmacy identifying information. Similar information can also be obtained using an RFID mechanism.

With the material identifier, along with other material information, obtained by the PCD 200, the PCD 200 can initiate a communications link with the proxy server 315 and transmit the identifier and/or other information along with a request for information regarding the identified material. It should be noted that the proxy server 315 can be programmed to listen for requests from the client PCD 200.

Once a request is received, the proxy server 315 can decode information provided therein. In one embodiment, the information can be formatted as a Universal Datagram Packet (UDP). For instance, the proxy server 315 can extract material identifiers, including any corresponding prescription numbers. If needed, the proxy server 315 can transcode the information into a suitable format for further transmission to the material supply server 310. With the extracted data, or the transcoded data, the proxy server 315 can contact the material supply server 310 at a known address or at an address provided in the UDP, such as the address of a material supply server 310 connected with a particular pharmacy.

Accordingly, the proxy server 315 can provide the material identifiers, along with the corresponding prescription number if needed, to the material supply server 310 via a Hypertext Transfer Protocol (HTTP) request. The user, or operator of the PCD 200, can be authenticated by the material supply server 310 through various identifications schemes, such as through information stored within the PCD 200 and/or scanned information or through a private key infrastructure (PKI) protocol. Additionally, it should be noted that further security and identification features, can also be provided using integrated circuit cards, such as a Java Card with an integrated microprocessor chip where applets are loaded into the memory of the microprocessor and run by the Java virtual machine or an ISO 7816 standard compliant smart card, either of which can be embedded in the PCD 200 and can provide additional programmatic capabilities. Upon successful authentication of the user if such security features are implemented, the material supply server 310 can provide the requested information. If the authentication is unsuccessful, the material supply server 310 can send a failure message to the PCD 200. Details of the failure can be provided to prompt the user to either adjust the request or to contact a healthcare professional for further assistance.

The material supply server 310 can provide requested information within an electronic document such as a document formatted using Wireless Markup Language (WML), Hypertext Markup Language (HTML), Extensible Markup Language (XML), or the like. The proxy server 315 can parse the received information and send the information to the PCD 200 in a format used by the PCD 200 client. For example, a full-color graphic image that is embedded within a document from the material supply server 310 can be transcoded into a grayscale image, in order to reduce the size of the information content before transmitting it from a proxy server 315 to the client 315 that has requested the document. Also, rich media, such as pictures, that are typically greater in size, can be removed before being transmitted to the PCD 200.

The information provided by the material supply server 310 can include calendaring information of when the patient should consume the material. For instance, the calendaring information may include the information that a user should take their insulin shots twice a day, and the calendaring software can be updated appropriately to provide adequate and timely reminders. Nevertheless, the information can also include other material information, such as general instructions of "take with food" and warnings about combining with other medications. If the user desires, the user can access this information using the display of the PCD 200. Since the material supply server 310 can be provided with particular material information, such as a prescription batch number, the material supply server 310 can provide particularized warnings such as if the prescription batch has been recalled.

In addition to using the PCD 200 to request and obtain updated material information, the PCD 200 can be used to simply identify materials. For instance, a user with limited sight may not be able to read a prescription bottle and, therefore, can use the wireless identification device of the PCD 200 to identify the contents of a package and/or container. As an example, the bar code reader of the PCD 200 can scan the barcode on the package to determine the particular material. The PCD 200 can provide a notification that the proper material has been identified and, in accordance with the material notification, provide confirmation that the user can consume the material. Still, the PCD 200 can simply display the name of the identified material and/or present instructions or supplemental relating thereto. In instances, where the material has been identified as inappropriate, the PCD 200 can provide a warning notification to the user to prevent the user from unintentionally consuming the wrong material.

The calendaring software of the PCD 200 can also record material consumption. For instance, after a reminder notification is provided to the user, the user can indicate whether a material was consumed. A log of material consumption can be maintained for access by healthcare professionals, such as a paramedic to determine whether a heart attack victim has consumed their required insulin.

Additionally, as the consumption of the materials is being recorded, the PCD 200 can also track the material quantity remaining for each material. The material quantity in a container can be provided to the PCD 200 via a bar code or a RFID tag, or can be provided from the material supply server 310 via the proxy 315. In either circumstance, when the material quantity reaches a predetermined threshold, for instance a week's supply of material, the PCD 200 can wirelessly contact the material supply server 310 and order additional material inventory for on location (i.e. home) delivery. For example, in one embodiment the material supply server 310 can be in communication with a pharmaceutical supply, such as a Web site, an automated phone service, or another network accessible system. Since the PCD 200 can automatically order additional material when the inventory diminishes, the PCD 200 can prevent an emergency situation where no material is available. In one arrangement, the PCD 200 can notify the user and obtain authorization before ordering additional inventory.

Thus, in accordance with the material information retrieved from the material supply server 310, the PCD 200 can remind the user, via an audio notification or a visual notification, to take particular medications at particular times and can remind a user to order or obtain a refill. Notably, the PCD 200 can require the user to respond to such reminders or notifications such that if no response is received, the PCD 200 can implement a programmatic action. For example, the PCD 200 can be programmed to contact a family member or a medical service provider, such as emergency medical services. Such persons can be contacted via a page, an electronic mail, a text message, and/or a programmed audio message via phone call.

Figure 4:
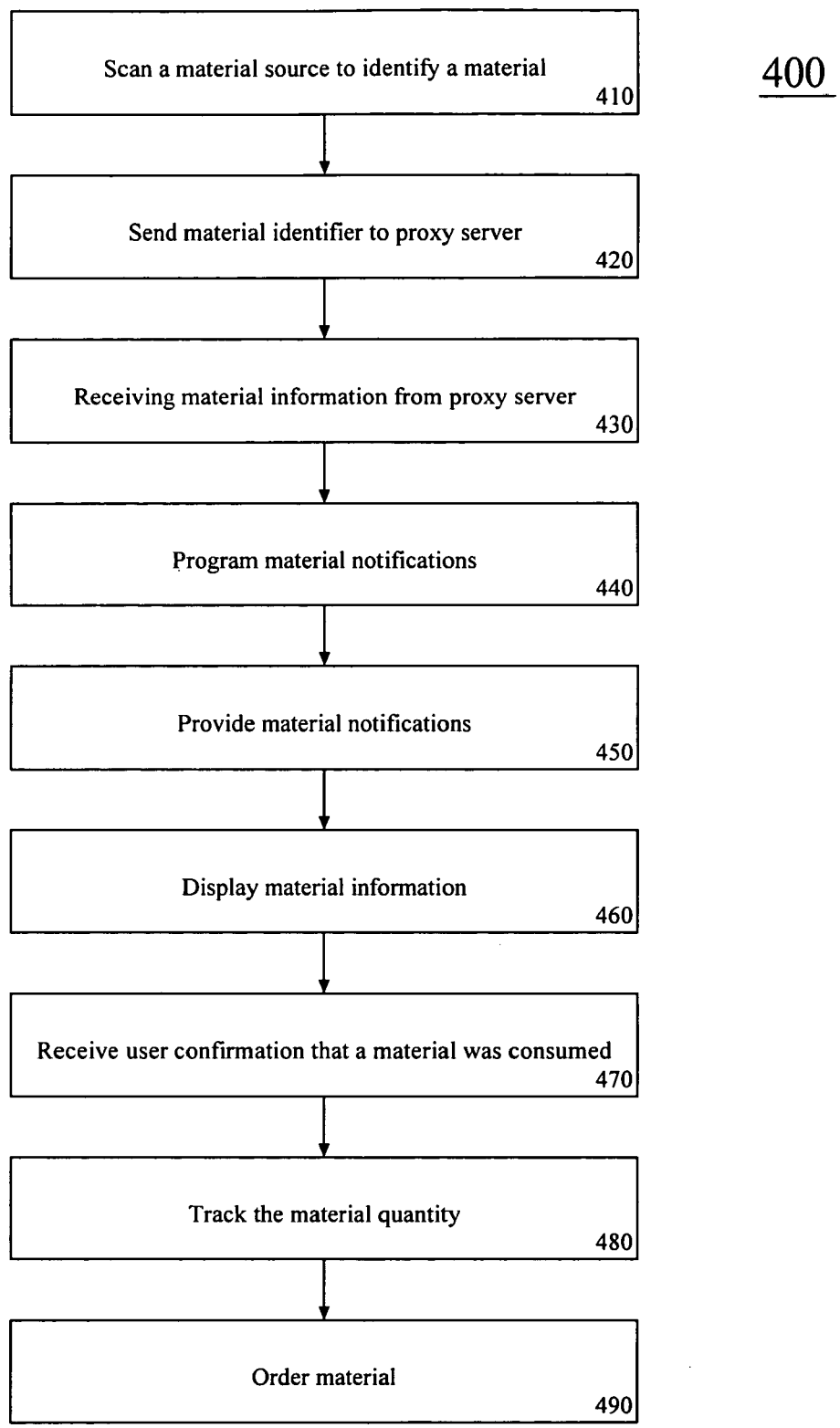
FIG. 4 is a flow chart illustrating a method for managing a material substance program.

Also in accordance with the inventive arrangements, a method for managing a material substance program is provided. Flow diagram FIG. 4. illustrates one exemplary arrangement of a method 400 for managing a material substance program. Although the flow diagram illustrates a sequence of steps, it should be noted that the steps can be completed in any order, and in many instances, one or more steps may be repeated. Further, it should be noted that some steps shown in FIG. 4 can be omitted while other steps can be included.

In step 410, a user can scan a material source to identify the material. Such scanning can include the use of a bar code reader, a RFID mechanism, and the like. Step 410 can be used either to simply identify the material for confirmation before consumption, or can be used to obtain material identifiers from the bar code and/or the RFID tag. For instance, the material identifiers can include prescription number, production plant, and pharmacy identifying information.

In step 420, the material identifiers, along with requests for additional information regarding the materials, can be sent, via wireless or wired transmissions, to a proxy server. For wireless transmissions, the transmissions can be sent over short range and/or long range wireless communication links. The material identifiers can be sent in a suitable format for access by the proxy server. With the material identifiers and requests, a material server can be contacted and requested to provide further information regarding the identified materials, such as calendaring instructions and/or usage instructions and warnings.

In step 430, the material information obtained or retrieved by the material server can be obtained by the PCD via the proxy server. The material information can be obtained in a format suitable for displaying on a PCD having mobile telephony capabilities.

In step 440, material notifications can be programmed in accordance with the information obtained. As an example, if the material information indicates that a particular medicine should be taken before bedtime, then a notification reminder automatically can be programmed to signal the user every night at 10:00 P.M. Other notifications, such as to "take with food", can be programmed to complement the reminder to take the material.

In step 450, the material notifications can be provided. They can be provided by signaling the user visually, audibly, physically, or using a combination of such indicators. For instance, the PCD can beep to signal the user to consume a specific material and the screen can display (step 460) any further instructions, warnings, or facts regarding the material. Also, it should be noted that the displaying of material information (step 460) is not limited to being conjunction with the material notifications, as the material information can be displayed at any time, such as when a user requests such information.

In step 470, the PCD can receive confirmation that a material was consumed. For instance, the user can actuate the input structure of the PCD to indicate that a material was consumed. It should be noted that notifications can be continued to be provided until the user signals that a material has been consumed.

In step 480, the material quantity can be tracked in order to maintain necessary levels of materials. With the material information received wirelessly in step 410, a known level of material inventory can be determined. Alternatively, material inventory level can be obtained in step 430. Further, with the scheduled notifications, the remaining inventory can be predicted as it should decrease over time in accordance with the scheduling. Nevertheless, some users may not always follow the scheduled program and, therefore in one arrangement, the remaining inventory count can be adjusted only when the user confirms (step 470) that a particular material was consumed. When the materials are identified and/or indicated as being consumed, the level of the known inventory can appropriately be reduced.

With the material quantity being tracked, material can be ordered at step 490. The predetermined level can be set according to material count, or any other appropriate indicator. When the material level reaches a predetermined level, a pharmacy or material source can be contacted and additional material can be order for home delivery. The pharmacy or material source can be contacted via wireless communication using the various arrangements and formats described herein.

Although the inventive arrangements disclosed herein have been described with reference to use by elder persons, people with poor eye site and/or hearing, it should be appreciated that such configurations also can be useful for other persons having physical or cognitive limitations and/or disabilities. Accordingly, the present invention should not be construed to be used solely for elder persons, or disabled persons for that matter.

Aspects of the present invention can be realized in hardware, software, or a combination of hardware and software. The present invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Each of the references cited herein is fully incorporated by reference.

What is claimed is:

1. A device for managing a material substance program, comprising:
    a portable computing device having a user interface and mobile telephony capabilities for transmitting a material identifier to a proxy server via a communications network, and for receiving material information regarding a material substance from a material supply server via the communications network, the material information corresponding to the material identifier;
    a calendar operated by said computing device for scheduling times that a user consumes the material substance, the scheduling based upon the received material information;
    a first notifier operated by said computing device for providing notifications to the user via said user interface based upon said calendar and reminding the user when the user is scheduled to consume the material substance;
    a recorder operated by the computing device for recording responses provided by the user via the user interface confirming when the user consumes the material substance at a scheduled time;
    a second notifier operated by said computing device for notifying a third-party when the user fails to provide a response within a predetermined interval after a notification is provided by said first notifier; and
    a wireless identification device communicably coupled to the portable computing device for identifying the material identifier prior to transmission of the material identifier to the proxy server.

2. The device according to claim 1, wherein the wireless identification device includes at least one of a bar code reader, a radio frequency identification mechanism, and a combination thereof.

3. The device according to claim 1, wherein the user interface of said portable computing device includes at least one of a display screen, an audible transducer, a vibration mechanism, and a combination thereof.

4. The device according to claim 1, wherein the portable computing device includes memory for storing material information.

5. A method for managing a material substance program, comprising the steps of:
    scanning a material source to identify a material identifier;
    sending the material identifier to a proxy server;
    receiving material information from the proxy server;
    based on the received material information, scheduling times that a user takes a material substance;
    based upon said calendar, providing intermittent notifications to the user via a user interface of a portable computing device having mobile telephony capabilities so as to remind the user when the user is scheduled to consume the material substance;
    recording responses provided by the user via the user interface confirming when the user consumes the material substance at a scheduled time; and
    notifying a third-party when the user fails to provide a response within a predetermined interval after the user receives an intermittent notification.

6. The method according to claim 5, further comprising the step of programming a material notification in accordance with the material information.

7. The method according to claim 1, wherein the step of providing notifications to the user includes at least one of displaying material information, audibly conveying the material information, initiating vibration of the portable computing device, and a combination thereof.

8. The method according to claim 5, further comprising the step of tracking the material quantity in accordance with consumption.

9. The method according to claim 8, further comprising the step of ordering material in accordance with the material quantity.

10. A machine-readable storage having stored thereon, a computer program having a plurality of code sections, said code sections executable by a machine for causing the machine to perform the steps of:
    scanning a material source to identify a material identifier;
    sending the material identifier to a proxy server;
    receiving material information from the proxy server;
    based on the received material information, scheduling times that a user takes a material substance;
    based upon said calendar, providing intermittent notifications to the user via a user interface of a portable computing device having mobile telephony capabilities so as to remind the user when the user is scheduled to consume the material substance;

recording responses provided by the user via the user interface confirming when the user consumes the material substance at a scheduled time; and notifying a third-party when the user fails to provide a response within a predetermined interval after the user receives an intermittent notification.

11. The machine readable storage according to claim 10, further comprising the step of programming a material notification in accordance with the material information.

12. The machine readable storage according to 10, wherein the step of providing notifications to the user includes at least one of displaying material information, audibly conveying the material information, initiating vibration of the portable computing device, and a combination thereof.

13. The machine readable storage according to claim 10, further comprising the step of tracking the material quantity in accordance with consumption.

14. The machine readable storage according to claim 13, further comprising the step of ordering material in accordance with the material quantity.

* * * * *